United States Patent

Hofmeister et al.

[11] 3,966,713
[45] June 29, 1976

[54] 11β-FLUOROANDROSTENES

[75] Inventors: Helmut Hofmeister; Henry Laurent; Rudolf Wiechert; Klaus Annen; Hermann Steinbeck, all of Berlin, Germany

[73] Assignee: Schering Aktiengesellschaft, Berlin & Bergkamen, Germany

[22] Filed: Feb. 25, 1975

[21] Appl. No.: 552,958

[30] Foreign Application Priority Data
Mar. 1, 1974 Germany.............................. 2410443

[52] U.S. Cl............... 260/239.55 R; 260/397.45; 260/397.3
[51] Int. Cl.² .......................................... C07C 3/00
[58] Field of Search................ 260/397.45; 424/238

[56] References Cited
UNITED STATES PATENTS

| | | | |
|---|---|---|---|
| 3,056,807 | 10/1962 | Ayer | 260/397.3 |
| 3,767,685 | 10/1973 | Van Vliet | 260/397.5 |
| 3,875,148 | 4/1975 | Elks et al. | 260/397.45 |

*Primary Examiner*—Elbert L. Roberts
*Attorney, Agent, or Firm*—Millen, Raptes & White

[57] ABSTRACT

11β-Fluoroandrostenes of the formula

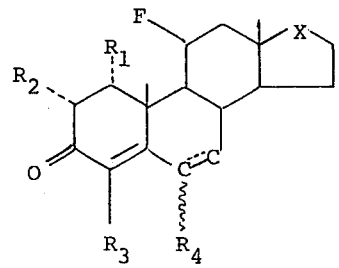

wherein $R_1$ and $R_2$ are hydrogen atoms, methylene or another C—C bond; $R_3$ is H or Cl, $R_4$ is H, F or Cl; and X is carbonyl, β-hydroxymethylene, or an ester or ether thereof or α-alkyl-β-hydroxymethylene or an ester thereof, possess androgenic activity and can be prepared by the dehalogenation of a corresponding 9α-halo-11β-F steroid.

38 Claims, No Drawings

11 BETA-FLUOROANDROSTENES

BACKGROUND OF THE INVENTION

This invention relates to novel 11β-fluoro steroids.

SUMMARY OF THE INVENTION

In a composition aspect, this invention relates to 11β-fluoroandrostenes of the general Formula I

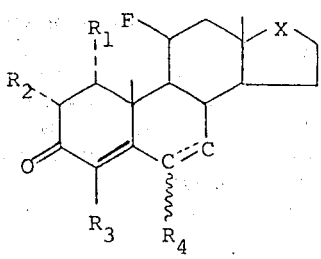

I wherein C═C is a single or double bond between the C-6 and C-7 carbon atoms; $R_1$ and $R_2$ are each a hydrogen atom or collectively are methylene or a further carbon-to-carbon bond between the C-1 and C-2 carbon atoms; $R_3$ is a hydrogen or chlorine atom; $R_4$ is a hydrogen, fluorine, or chlorine atom; and X is carbonyl, β-hydroxymethylene or an ether or ester thereof, or α-allyl-β-hydroxymethylene or an ester thereof in which the alkyl group is saturated or unsaturated and/or unsubstituted or substituted, e.g., one of the groups

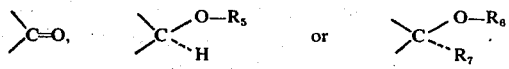

wherein $R_5$ is a hydrogen atom or acyl, alkyl, or an oxygen-heterocyclic group, $R_6$ is a hydrogen atom or acyl and $R_7$ is substituted or unsubstituted, saturated or unsaturated alkyl.

In another composition aspect, this invention relates to pharmaceutical compositions comprising one or more compounds of this invention.

In process aspects, this invention relates to the production and use as androgens of the compounds of this invention.

DETAILED DISCUSSION

Since the pharmacological activity resides in the steroid moiety, equivalents of the compounds of this invention wherein X is β-hydroxymethylene or α-alkyl-β-hydroxymethylene are esters and ethers of those compounds. The exact nature of the ester and ether groups is not critical.

Thus, suitable acyl $R_5$ and $R_6$ groups are the physiologically acceptable acyl groups of acids customarily employed for the esterification of steroid alcohols. Among these are the organic carboxylic acids, inter alia, those of 1-18 carbon atoms, preferably 1-11 carbon atoms, of the aliphatic, alicyclic, aromatic, and heterocyclic series, including those which are saturated or unsaturated, mono-, di- or polybasic, and unsubstituted or substituted, e.g., by alkyl, hydroxy, oxo, or amino groups, or halogen atoms. Other equivalents are esters of the customary inorganic acids and sulfonic acids.

Examples of suitable carboxylic acids are lower, intermediate, and higher hydrocarbon carboxylic acids, preferably those of up to 16 carbon atoms, including formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, palmitic acid, trimethylacetic acid, diethylacetic acid, tert.- butylacetic acid, cyclopentylacetic acid, cyclopentylpropionic acid, cyclohexylacetic acid, mono-, di-, and trichloroacetic acid, aminoacetic acid, diethylaminoacetic acid, piperidinoacetic acid, morpholinoacetic acid, lactic acid, succinic acid, adipic acid, benzoic acid, nicotinic acid, isonicotinic acid, furan-2-carboxylic acid.

Examples of suitable esters of conventional inorganic acids are esters of sulfuric acid and phosphoric acid. Examples of esters of sulfonic esters are those of benzene-p-toluene-, methane-, and ethanesulfonic acid.

To produce water-soluble preparations, the acids usually employed for the formation of water-soluble esters are suitable. Examples are succinic acid, adipic acid, sulfuric acid, and phosphoric acid, the monoesters of which are optionally converted into the alkali metal salts, e.g., the potassium or sodium salt.

Suitable $R_5$ alkyls are those of up to 6 carbon atoms, preferably of up to 4 carbon atoms, including methyl, ethyl, or butyl residue. Also suitable as the alkyl residues $R_5$ are also cycloalkyl residues of up to 7 carbon atoms, preferably those of 5 or 6 carbon atoms.

Ethers wherein $R_5$ is an oxygen-containing heterocyclic group includes those wherein $R_5$ is an unsaturated or saturated oxygen heterocyclic group. Examples are the tetrahydropyranyl which can optionally be further substituted by a hydroxy or lower alkyl group of up to 4 carbon atoms, and 5,6-dihydro-2H-pyran-4-yl.

$R_7$ alkyl groups include those of up to 7 carbon atoms, including saturated and unsaturated alkyl of 1-5 carbon atoms, e.g., methyl, ethyl, butyl, vinyl, ethinyl, propinyl and butadiynyl, preferably ethinyl. These alkyl groups can also be substituted in a conventional way with chloroethinyl being preferred.

Compounds of this invention possess valuable steroid hormone properties and thus can be used as pharmaceuticals. Accordingly, the utilization of the compunds of this invention as medicinal agents or as a constituent thereof is also the subject matter of this invention. Thus, the steroids of Formula I exhibit, inter alia, strong androgenic activity. For example, 17β-acetoxy-11β-fluoro-4-androsten-3-one is superior to the standard compound testosterone acetate in the conventional seminal vesicle, prostate, and musculus levator ani test. The compounds of this invention also exhibit anabolic and progestational activities. The longer-chain esters are distinguished by protracted activity.

Usual conventional pharmaceutically acceptable carriers, excipients and additives, drug specialties for oral, parenteral and other modes of administration can be produced from the compounds of Formula I in the usual manner. Suitable additives are the vehicles, diluents, flavor-ameliorating agents, etc. customary in galenic pharmacy. The effective agents can be processes, for example, into intramuscular applicable oily injection solutions or into tablets, capsules, etc.

In medical practice, the androgenic medicinal agents of the present invention can be utilized, for example, for the treatment of diseases caused by an androgen deficiency. The treatment of the following illnesses can be considered a field of use of these compounds:

In the human male:

Hypogonadism, sterility, disturbances in potency, climacterium virile, cardiac complaints, pectoral-anginoid disturbances, depressive conditions, pruritus senilis, debilitated general condition in case of protein deficiency, cachexia, preparation for operations and postoperative treatment, cirrhosis of the liver, osteoporosis, retarded healing of fractures, aplastic anemias.

In the human female:

Climacterium, mastopathia cystica, frigidity.

The novel compounds of this invention can be administered in the same manner as testosterone acetate, but usually in lower dosages because of their higher androgenic activity.

This invention also relates to a process for the production of compounds of general Formula I, wherein a 9-halo-11β-fluoroandrostene of the general Formula II

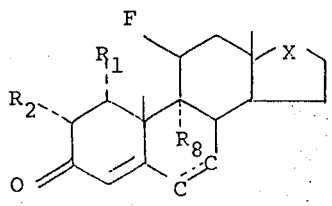

wherein $R_1$, $R_2$, X and C≡C have the values given for Formula I and $R_8$ is a halogen atom, is dehalogenated; and thereafter, if desired, depending on the desired final value for $R_1$, $R_2$, $R_3$, $R_4$, X, and C≡C, introducing a chlorine atom into the 4-position; and/or introducing a fluorine atom or a chlorine atom into the 6-position; and/or introducing a double bond into the 1- and/or 6-position and optionally thereafter, a methylene into the 1α,2α-position; and/or reducing the 17-keto group, optionally after masking the 3-keto group, hydrogenating an unsaturated 17α-alkyl group, splitting off a keto masking group; and/or esterifying or etherifying a free hydroxy group or hydrolyzing an esterified or etherified hydroxy group. Suitable $R_8$ halogen atoms are chlorine and bromine atoms.

It is known that 9α-bromo-11β-hydroxy-4-pregnene-3,20-dione can be debrominated with triphenyltin hydride [Barton et al., J. Amer. Chem. Soc. 88 (1966) 3016]. If this reaction is conducted with a corresponding 6-fluoro compound, the 6-fluorine atom is also replaced by hydrogen along with the halogen atom in the 9-position. Thus, for purposes of dehalogenating 6-fluoro-9-bromo-11β-hydroxy steroids, it is necessary to conduct the elimination of the 9-halogen atom solely with trialkyltin hydrides to avoid an attack on the fluorine atom in the 6-position.

It has now been found, surprisingly, that only the 9α-positioned halogen atom is selectively eliminated from 11β-fluoro-9-halogen-4-androsten-3-ones with both trialkyltin hydrides and triaryltin hydrides without the 11β-fluorine atom being attacked.

It would have been expected, analogously to the reaction of the 6-fluoro-9-halopregnanes that at least during the reaction with triaryltin hydrides, the 11-fluorine atom would be split off.

The process of this invention is suitably conducted by dissolving the starting steroid in a suitable inert solvent and adding the trialkyl- or triaryltin hydride.

Examples of suitable trialkyltin hydrides are those wherein the alkyl groups are of 1–4 carbon atoms, e.g., trimethyltin hydride, triethyltin hydride, and tributyltin hydride, the latter being preferred because it can be handled relatively simply.

Examples of suitable triaryltin hydrides are the tin hydrides of the mononuclear aromatics, such as alkyl($C_1$–$C_4$)phenyl-, phenylalkyl ($C_1$–$C_4$) tin hydrides, wherein the alkyl or phenyl group can be in any desired position, and triphenyltin hydride, the latter being preferred.

The reaction is preferably conducted in the presence of a radical-forming agent, but this does not exclude the possibility of performing the reaction without such agent, in which case, longer reaction times may be necessary. Suitable radical-forming agents are, for example, azodiisobutyrodinitrile, di-tert.-butyl peroxide. The reaction can also be effected under UV radiation.

The process of this invention can optionally also be conducted by forming the trialkyltin hydride in situ during the reaction. For this purpose, the corresponding trialkyltin oxide and polymethyl siloxane are added to the dissolved starting steroid. The advantage of this variant of the process is that readily decomposed trialkyltin hydrides need not be isolated.

Suitable solvents for the process of this invention are those inert with respect to the reactants. Examples are acyclic ethers, e.g., diethyl ether and glycol ether, cyclic ethers, e.g., tetrahydrofuran and dioxane, and hydrocarbons, e.g., hexane and benzene. Also suitable are alcohols, e.g., ethanol and glycol, and nitriles, e.g., acetonitrile.

The process of this invention is advantageously accomplished at about room temperature. However, this process can also be conducted at temperatures above room temperature, the upper temperature limit being the boiling point of the reaction mixture. The reaction also takes place below room temperature but reaction times can sometimes be very long.

The conductance of one or more of the optional subsequent reactions can be in accordance with the methods known in the art. Examples are:

For the introduction of the chlorine atom in the 4-position, reaction with sulfuryl chloride or chlorine in the presence of a proton acceptor, e.g., a nitrogen-containing heterocyclic base, such as pyridine or picoline, or in the absence of the proton acceptor, with subsequent treatment with the proton acceptor;

for the introduction of the fluorine or chlorine atom in the 6-position, reaction with an N-chlorimide, e.g., N-chlorosuccinimide, or with elemental chlorine, or conversion into a 3-enol ester or enol ether, such as the 3-enolethyl ether or the 3-enolacetate, and subsequent reaction with chlorine, an N-chlorimide, or perchloryl fluoride;

for the simultaneous introduction of a Δ⁶-double bond and a fluorine or chlorine atom, conversion into the 6,7-epoxide, e.g., by treatment with a peracid, such as m-chloroperbenzoic acid, etc., treatment of the epoxide with hydrogen chloride (fluoride), and splitting off water from the thus-obtained 7-hydroxy-6-chloro(-fluoro)-steroid while eliminating the 7-hydroxy group and introducing the Δ⁶-double bond;

for the introduction of the Δ¹-double bond, the reaction with chloranil or 2,3-dichloro-5,6-dicyano-1,4-benzoquinone or the dehydrogenation with selenium compounds, e.g., selenium dioxide or selenous acid, or the microbiological Δ¹-introduction;

for the introduction of the $\Delta^6$-double bond, the reaction with chloranil or 2,3-dichloro-5,6-dicyano-1,4-benzoquinone or the bromination with N-bromosuccinimide with subsequent hydrogen bromide cleavage by means of lithium halide and alkali metal carbonate;

for the simultaneous introduction of the $\Delta^1$- and $\Delta^6$- double bonds, the reaction with chloranil or the bromination by means of bromine to the 2,6-dibromo derivative with subsequent debromination with lithium halide and alkali metal carbonate;

for introducing the methylene group, the reaction with dimethyl sulfoxonium methylide or the reaction with diazomethane with subsequent thermal or catalytic splitting of the thus-formed 1',2'-pyrazolino steroids;

for reducing the 17-keto group, reaction with hydrogen in the presence of customary catalysts or reaction with organometallic compounds in the usual solvents;

for the esterification, reaction with acid anhydrides in the presence of strong acids, e.g., p-toluenesulfonic acid, or reaction with acid anhydrides in the presence of a tertiary amine under heating;

for the etherification, reaction with a (cyclo) alkyl halogenide in the presence of a mild base, e.g., silver oxide, or reaction of the hydroxy steroid with the oxygen-containing heterocyclic compound, for example, tetrahydropyran, in the presence of an acidic catalyst, e.g., p-toluenesulfonic acid, etc., in inert organic solvents;

for the hydrolysis, reaction of the esters with alkali metal carbonates or hydroxides in an aqueous-alcoholic solution, optionally at an elevated temperature, or reaction of the tetrahydropyranyl ethers with oxalic acid in a aqueous-alcoholic solution at an elevated temperature, or reaction of the alkyl ethers with hydrogen halides in the usual solvents.

The 17-keto group can be reduced, for example, by hydrogenation with a metal hydride. Especially suitable hydrogen donors proved to be complex hydrides, for example, sodium hydridoborate, lithium hydridoaluminate, sodium hydridotrimethoxoborate, and lithium hydrido-tri-tert.-butoxoaluminate. The reduction can also be conducted according to conventional methods with an organometallic compound wherein the organic residue is $R_7$ and wherein this compound can be an alkylmagnesium halide, e.g., methylmagnesium bromide or iodide; an alkenylmagnesium and/or alkenylzinc halide, e.g., vinylmagnesium bromide or allylmagnesium bromide; an alkinyl-magnesium halide, such as ethinylmagnesium bromide, propinyl-magnesium bromide, or propinylzinc bromide; or an alkali metal acetylide, such as potassium acetylide. The organometallic compound employed as the reducing agent can also be formed in situ and and reacted with the 17-ketone of Formula II. Thus, the ketone is treated, for example, to react same with organometallic alkinyl compounds, in a suitable solvent with an alkine, chloroalkine, or alkadiyne and an alkali metal, preferably in the presence of a tertiary alcohol or of ammonia, optionally under elevated pressure.

The reduction of the 17-keto group is conducted, in a preferred embodiment, with a masked 3-keto group being present. Suitable processes for protecting the 3-keto group are conventional methods, such as enol ester, enol ether, and ketal formation. The enol ester formation can be attained, for example, by treatment with an acylating agent, such as isopropenyl acetate, in the presence of a catalyst, such as p-toluenesulfonic acid. The enol ether formation can be accomplished, for example, by reaction with an orthoformic acid ester in the presence of a catalyst such as ethyl orthoformate, in the presence of hydrochloric acid. For purposes of ketalization, the 3-keto steroid is reacted with the alcohols customarily used for the masking of free oxo groups, e.g., ethylene glycol and 2,2-dimethyl-1,3-propanediol, in the presence of an acidic catalyst, for example, p-toluenesulfonic acid. The thus-introduced unsaturated 17α-alkyl residues can be converted, by hydrogenation, into the corresponding 17α-alkenyl and 17α-alkyl steroids, respectively. As is known, this hydrogenation is preferably conducted by reacting steroids with an unsaturated 17α-alkyl residue with hydrogen in the presence of a hydrogenation catalyst. Examples of suitable hydrogenation catalysts are palladium catalysts or platinum oxide catalysts, on supports, if desired.

The splitting off of the 3-keto masking group takes place according to methods known to a person skilled in the art. For purposes of deketalization, it is possible to employ, for example, mineral acids, e.g., perchloric acid, etc., or organic acids, such as oxalic acid. The conversion of the 3-enol ether or 3-enol ester grouping into the 3-keto-$\Delta^4$-grouping is accomplished with the aid of conventional hydrolysis reactions.

Insofar as isomeric mixtures are formed during the aforedescribed chlorinations and fluorinations, respectively, i.e., mixtures of 6α- and 6β-chloro(fluoro) steroids, these can be separated into the pure isomers by means of conventional methods, such as chromatography, etc.

The isomerization of a thus-obtained 6β-fluoro- or -chloro-compound can be accomplished by treatment with an acid, especially a mineral acid, such as hydrochloric acid, or hydrobromic acid in a solvent, e.g., dioxane or glacial acetic acid.

The preparation of the 9-halo-11β-fluoroandrostenes of general Formula II utilized as the starting compounds is illustrated below.

17β-acetoxy-9-bromo-11β-fluoro-4-androsten-3-one (A)

9-bromo-11β-fluoro-4-androstene-3,17-dione (B)

17β-acetoxy-9-chloro-11β-fluoro-4-androsten-3-one (C)

17β-acetoxy-9-bromo-11β-fluoro-4,6-androstadien-3-one (D)

9-chloro-11β-fluoro-4-androstene-3,17-dione (E) and

17β-acetoxy-9-bromo-11β-fluoro-1,4,6-androstatrien-3-one (F).

Analogously, starting compounds of Formula II with other desired meanings of the substituents can be produced by means of methods known to persons skilled in the art.

The temperatures set forth below are indicated in degrees Celsius.

A:

17β-Acetoxy-9-bromo-11β-fluoro-4-androsten-3-one

At −78°, 80 ml. of hydrogen fluoride is combined with 32 ml. of dimethylformamide, 22 g. of 17β-acetoxy-4,9(11)-androstadien-3-one, and 16 g. of N-bromosuccinimide. The mixture is allowed to stand for 1.5 hours at −30° and then introduced into a mixture of ice/water and a 25% ammonia solution. The precipitate is filtered off, dissolved in a mixture of ethyl acetate and methylene chloride, washed with water, and dried over sodium sulfate. After chromatography with acetone/hexane, 9.1 g of 17β-acetoxy-9-bromo-11β-fluoro-4-androsten-3-one is obtained; m.p. 172°–174° UV: $\epsilon_{239}$ = 16,300 (methanol).

B:

9-Bromo-11β-fluoro-4-androstene-3,17-dione

At −78°, 100 ml. of hydrogen fluoride is combined with 40 ml. of dimethylformamide, 20 g. of N-bromosuccinimide, and 27 g. of 4,9(11)-androstadiene-3,17-dione. The reaction mixture is agitated for 4.5 hours at −30° and then introduced into a mixture of ice/water and a 25% ammonia solution. After the reaction mixture has been worked up as described in Example A, the product is chromatographed on silica gel with acetone/methylene chloride, yielding 17.3 g. of 9-bromo-11β-fluoro-4-androstene-3,17-dione; m.p. 165°–166°. UV: $\epsilon_{239}$ = 17,500 (methanol).

C:

17β-Acetoxy-9-chloro-11β-fluoro-4-androsten-3-one

At −78°, a mixture of 10 ml. of hydrogen fluoride and 3 ml. of N-methylpyrrolidone is combined, in sequence, with 3.0 g. of 17β-acetoxy-4,9(11)-androstadien-3-one and 6.0 g. of N-chlorosuccinimide. The reaction solution is held at +3 for 25 hours and then poured into a mixture of ice/water and a 25% ammonia solution. The thus-precipitated product is vacuum-filtered and worked up as set forth in Example A. Chromatography on silica gel with acetone/hexane yields 1.2 g. of 17β-acetoxy-9-chloro-11β-fluoro-4-androsten-3-one as a foamy product. UV: $\epsilon_{239}$ = 16,500 (methanol).

D:

17β-Acetoxy-9-bromo-11β-fluoro-4,6-androstadien-3-one 2.3 g. of 17β-acetoxy-9-bromo-11β-fluoro-4-androsten-3-one is agitated for 8 hours under reflux with a mixture of 25 ml. of tert.-butanol and 15 ml. of ethylene chloride with 4 g. of chloranil and 50 g. of p-toluenesulfonic acid. The product is then filtered off from the insoluble matter, the filtrate is diluted with ether and washed successively with 2N sodium hydroxide solution and water. The crude product is chromatographed on silica gel with acetone/-hexane, yielding 1.1 g. of 17β-acetoxy-9-bromo-11β-fluoro-4,6-androstadien-3-one as a foamy product. UV: $\epsilon_{280}$ = 26,300 (methanol).

E:

9-Chloro-11β-fluoro-4-androstene-3,17-dione

At −78°, a mixture of 15 ml. of hydrogen fluoride and 5 ml. of N-methylpyrrolidone is combined successively with 5.1 g of 4,9(11)-androstadiene-3,17-dione and 10 g. of N-chlorosuccinimide. The reaction solution is allowed to stand for 2 days at +3° and then introduced into a mixture of ice/water and a 25% ammonia solution. The thus-precipitated product is worked up as set forth in Example A. After chromatography of the crude product on silica gel with acetone/hexane, 1.6 g. of 9-chloro-11β-fluoro-4-androstene-3,17-dione is isolated as an oil. UV: $\epsilon_{239}$ = 16,200 (methanol).

F:

17β-Acetoxy-9-bromo-11β-fluoro-1,4,6-androstatrien-3-one 800 mg. of 17β-acetoxy-9-bromo-11β-fluoro-4,6-androstadien-3-one is stirred under reflux in 4 ml. of benzene with 1.0 g. of 2,3-dichloro-5,6-dicyano-1,4-benzoquinone for 5 hours. The reaction mixture is diluted with ether and washed repeatedly and successively with 2N sodium hydroxide solution and water. The solution is dried over sodium sulfate. The crude product is chromatographed on silica gel with acetone/hexane, yielding 290 mg. of 17β-acetoxy-9-bromo-11β-fluoro-1,4,6-androstatrien-3-one as a foamy product. UV: $\epsilon_{299}$ = 12,200 (methanol).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

8 g. of 17β-acetoxy-9-bromo-11β-fluoro-4-androsten-3-one is agitated at room temperature for 5 hours in 160 ml. of tetrahydrofuran with 20 ml. of tributyltin hydride with the addition of 10 mg. of α,α'-azoisobutyrodinitrile. The solution is evaporated under vacuum; the residue is crystallized with hexane. The crystalline product is vacuum-filtered and chromatographed on silica gel for further purification. With ethyl acetate/hexane, 3.4 g. of 17β-acetoxy-11β-fluoro-4-androsten-3-one is obtained as the elution product; m.p. 165°–167° (decomposition). UV: $\epsilon_{239}$ = 16,400 (methanol).

EXAMPLE 2

One gram of 17β-acetoxy-11β-fluoro-4-androsten-3-one is heated under reflux in 5 ml. of benzene with 1.0 g. of 2,3-dichloro-5,6-dicyano-1,4-benzoquinone for 6 hours. The reaction mixture is diluted with ether and washed successively several times with 2N sodium hydroxide solution and water. The solution is dried and evaporated under vacuum. Recrystallization of the crude product from acetone/hexane yields 600 mg. of 17β-acetoxy-11β-fluoro-1,4-androstadien-3-one; m.p. 164°–165°. UV: $\epsilon_{241}$ = 15,800 (methanol).

EXAMPLE 3

1.2 g. of 17β-acetoxy-11β-fluoro-4-androsten-3-one is stirred in a mixture of 30 ml. of methanol and 5 ml. of water for 10 hours at room temperature with 1 g. of potassium carbonate. The reaction mixture is filtered off from the insoluble matter, the solution is neutralized with glacial acetic acid, concentrated under vacuum, the residue taken up in methylene chloride, and dried. After recrystallization from acetone/hexane, 800 mg. of 11β-fluoro-17β-hydroxy-4-androsten-3-one is obtained; m.p. 161°–162°. UV: $\epsilon_{239}$ = 16,600 (methanol).

EXAMPLE 4

530 mg. of 11β-fluoro-17β-hydroxy-4-androsten-3-one is heated in 3 ml. of pyridine with 1 ml. of enanthic acid anhydride for 3 hours to 120°. The solution is diluted with benzene and subjected to steam distillation. The reaction product is extracted from the aqueous distillation residue with methylene chloride. Chromatography of the crude product on silica gel with acetone/hexane yields 410 mg. of 11β-fluoro-17β-heptanoyloxy-4-androsten-3-one as an oily compound. UV: $\epsilon_{239}$ = 15,900 (methanol).

EXAMPLE 5

350 mg. of 11β-fluoro-17β-hydroxy-4-androsten-3-one is stirred for 3 hours at 120° in 2 ml. of pyridine with 1 ml. of cyclopentylpropionic acid anhydride. The solution is worked up as described in Example 4. Chromatography of the crude product on silica gel with acetone/hexane yields 230 mg. of 11β-fluoro-17β-(3'-cyclopentylpropionyloxy)-4-androsten-3-one as an oil. UV: $\epsilon_{239} = 15,700$ (methanol).

EXAMPLE 6

650 mg. of 11β-fluoro-17β-hydroxy-4-androsten-3-one is stirred for 15 hours at room temperature in 15 ml. of absolute benzene with 2 ml. of triethylamine and 0.5 ml. of capric acid chloride. The solution is diluted with ether and washed successively with sodium bicarbonate solution, water, dilute sulfuric acid, and water. The solution is dried over sodium sulfate and evaporated under vacuum, yielding 390 mg. of 11β-fluoro-17β-decanoyloxy-4-androsten-3-one as an oily product. UV: $\epsilon_{239} = 15,600$ (methanol).

EXAMPLE 7

460 mg. of 11β-fluoro-17β-hydroxy-4-androsten-3-one is combined in 4 ml. of pyridine with 4 ml. of benzoyl chloride and agitated at room temperature for 2 hours. The solution is stirred into ice/water. The thus-precipitated product is vacuum-filtered, taken up in methylene chloride, washed successively with dilute sulfuric acid, water, and sodium bicarbonate solution, and dried over sodium sulfate. Recrystallization from acetone/hexane yields 180 mg. of 17β-benzoyloxy-11β-fluoro-4-androsten-3-one; m.p. 152°-155°. UV: $\epsilon_{239} = 16,100$ (methanol).

EXAMPLE 8

800 mg. of 11β-fluoro-17β-hydroxy-4-androsten-3-one is stirred under reflux in 35 ml. of absolute benzene with 10 ml. of methyl iodide and 2 g. of silver oxide for 10 hours. The mixture is filtered off from the insoluble matter, the filtrate is evaporated under vacuum, and the reaction product is taken up in methylene chloride. Purification by preparative layer chromatography (hexane/ethyl acetate 7 : 3) yields 180 mg. of 11β-fluoro-17β-methoxy-4-androsten-3-one. UV: $\epsilon_{239} = 15,800$ (methanol).

EXAMPLE 9

350 mg. of 11β-fluoro-17β-hydroxy-4-androsten-3-one is stirred under reflux in 20 ml. of absolute benzene with 5 ml. of butyl iodide and 1 g. of silver oxide for 10 hours. The reaction mixture is filtered off from the insoluble matter and worked up as described in Example 8. The crude product is purified with the aid of preparative layer chromatography (hexane/ethyl acetate 7 : 3), thus isolating 73 mg. of 11β-fluoro-17β-butoxy-4-androsten-3-one as an oily product. UV: $\epsilon_{239} = 16,100$ (methanol).

EXAMPLE 10

1.5 g. of 11β-fluoro-17β-hydroxy-4-androsten-3-one is allowed to stand for 6 hours at room temperature in 50 ml. of tetrahydrofuran with 5 ml. of dihydropyran and 2 drops of phosphorus oxychloride. The solution is stirred into ice/water. The thus-precipitated product is filtered, washed with water, taken up in methylene chloride, and dried over sodium sulfate. After the solvent has been distilled off under vacuum, the yield is 1.6 g. of 1.6 g. of 11β-fluoro-17β-tetrahydropyranyloxy-4-androsten-3-one as an oily product. UV: $\epsilon_{239} = 15,600$ (methanol).

EXAMPLE 11

5.7 g. of 9-bromo-11β-fluoro-4-androstene-3,17-dione is stirred in 120 ml. of tetrahydrofuran with 15 ml. of triphenyltin hydride at room temperature for 24 hours, with the addition of 10 mg. of α,α'-azoisobutyrodinitrile. After the reaction mixture has been worked up as set forth in Example 1, it is chromatographed on silica gel with acetone/methylene chloride, thus obtaining 2.1 g. of 11β-fluoro-4-androstene-3,17-dione; m.p. 165°-166° (acetone/hexane). UV: $\epsilon_{238} = 16,600$ (methanol).

EXAMPLE 12

At —70°, 600 mg. of potassium is introduced in incremental portions into 50 ml. of liquid ammonia while passing a weak acetylene stream through the mixture. Thereafter, the acetylene stream is increased. As soon as all of the potassium has been reacted to the acetylide, a solution of 1.5 g. of 11β-fluoro-4-androstene-3,17-dione in a mixture of 10 ml. of benzene and 10 ml. of ether is added under agitation. The solution is allowed to stand for 3 hours at the indicated temperature and then for 10 hours at room temperature. Then, the solution is diluted with ether, washed repeatedly with water, and dried. Chromatography of the crude product on silica gel with acetone/hexane yields 1.1 g. of 17α-ethinyl-11β-fluoro-17β-hydroxy-4-androsten-3-one. UV: $\epsilon_{239} = 16,800$ (methanol).

EXAMPLE 13

A solution of 1.0 g. of 17α-ethinyl-11β-fluoro-17β-hydroxy-4-androsten-3-one in 10 ml. of collidine and 4 ml. of acetic anhydride is heated under nitrogen for 2 hours. After cooling, the reaction mixture is poured into water and then subjected to steam distillation. The residue is taken up in methylene chloride, and the extract is washed with water. The crude product is chromatographed on silica gel with acetone/hexane, yielding 280 mg. of 17β-acetoxy-17α-ethinyl-11β-fluoro-4-androsten-3-one as an oil. UV: $\epsilon_{239} = 16,200$ (methanol).

EXAMPLE 14

A solution of 750 mg. of 17α-ethinyl-11β-fluoro-17β-hydroxy-4-androsten-3-one in 8 ml. of collidine and 3 ml. of enanthic acid anhydride is heated for 4 hours to the boiling point under nitrogen and then, after cooling, worked up as set forth in Example 13. Chromatography of the crude product on silica gel with acetone/hexane yields 125 mg. of 17α-ethinyl-11β-fluoro-17β-heptanoyloxy-4-androsten-3-one as an oil. UV: $\epsilon_{239} = 16,000$ (methanol).

EXAMPLE 15

From a solution of 4 g. of palmitic acid in 170 ml. of benzene, 30 ml. is removed by distillation. After cooling to room temperature, the mixture is combined with 2.2 ml. of trifluoroacetic acid anhydride and stirred for 30 minutes. Then, 2 g. of 17α-ethinyl-11β-fluoro-17β-hydroxy-4-androsten-3-one is added thereto and the mixture agitated for another 3 hours at room temperature. The reaction mixture is combined with a small amount of water and thereafter extensively concentrated under vacuum. The residue is taken up in methylene chloride and washed successively with 10% sodium hydroxide solution and water. The crude product is chromatographed on silica gel with ethyl acetate/hexane, yielding 950 mg. of 17α-ethinyl-11β-fluoro-17β-hexadecanoyloxy-4-androsten-3-one as an oil. UV: $\epsilon_{236} = 16,300$ (methanol).

EXAMPLE 16

5 g. of 17β-acetoxy-11β-fluoro-4-androsten-3-one is stirred under reflux in a mixture of 50 ml. of tert.-butanol and 30 ml. of ethylene chloride with 8 g. of chloranil and 100 mg. of p-toluenesulfonic acid for 7 hours. The mixture is filtered off from the insoluble matter, the filtrate is diluted with ether and washed in sequence with 2N sodium hydroxide and water. The crude product is chromatographed on silica gel with acetone/hexane, thus obtaining 1.8 g. of 17β-acetoxy-11β-fluoro-4,6-androstadien-3-one as a foamy product. UV: $\epsilon_{280} = 26,100$ (methanol).

EXAMPLE 17

15 g. of m-chloroperbenzoic acid in 75 ml. of tert.-butanol and 15 ml. of ethylene chloride is added to 3 g. of 17β-acetoxy-11β-fluoro-4,6-androstadien-3-one in 180 ml. of ethylene chloride. The solution is allowed to stand at room temperature for 48 hours, then diluted with ethyl acetate, and washed successively with sodium bisulfite solution and water. Yield: 1.3 g. of 17β-acetoxy-6α,7α-epoxy-11β-fluoro-4-androsten-3-one as an oily product. UV: $\epsilon_{239} = 15,800$ (methanol).

500 mg. of 17β-acetoxy-6α,7α-epoxy-11β-fluoro-4-androsten-3-one is introduced at room temperature into 25 ml. of glacial acetic acid saturated with gaseous hydrogen chloride. After 24 hours, the solution is poured into ice/water. The thus-precipitated product is vacuum-filtered, taken up in methylene chloride, washed with water, and dried. After recrystallization of the crude product from acetone/hexane, 210 mg. of 17β-acetoxy-6-chloro-11β-fluoro-4,6-androstadien-3-one is obtained. UV: $\epsilon_{283} = 20,300$.

EXAMPLE 18

2.3 g. of 11β-fluoro-4-androstene-3,17-dione is stirred under reflux in 25 ml. of tert.-butanol and 15 ml. of ethylene chloride with 4 g. of chloranil and 50 mg. of p-toluenesulfonic acid for 6 hours. After the reaction mixture has been worked up as described in Example 16 and chromatographed on silica gel with acetone/hexane, 1.2 g. of 11β-fluoro-4,6-androstadiene-3,17-dione is obtained. UV: $\epsilon_{280} = 25,600$.

EXAMPLE 19

1.3 g. of 11β-fluoro-4,6-androstadiene-3,17-dione is reacted analogously to Example 12 with 600 mg. of potassium in 50 ml. of liquid ammonia while passing acetylene through the reaction mixture. The crude product is chromatographed on silica gel with acetone/hexane, yielding 870 mg. of 17α-ethinyl-11β-fluoro-17β-hydroxy-4,6-androstadien-3-one. UV: $\epsilon_{280} = 25,900$ (methanol).

EXAMPLE 20

750 mg. of 17α-ethinyl-11β-fluoro-17β-hydroxy-4,6-androstadien-3-one in 50 ml. of ethylene chloride is combined with 1.2 g. of m-chloroperbenzoic acid in 5 ml. of tert.-butanol and 1 ml. of ethylene chloride. The mixture is agitated at room temperature for 21 hours. The solution is then diluted with ethyl acetate and washed successively with sodium bisulfite solution and water. In this way, 420 mg. of 17α-ethinyl-6α,7α-epoxy-11β-fluoro-17β-hydroxy-4-androsten-3-one is isolated. UV: $\epsilon_{239} = 16,300$ (methanol).

460 mg. of 17α-ethinyl-6α,7α-epoxy-11β-fluoro-17β-hydroxy-4-androsten-3-one is introduced at room temperature into 25 ml. of glacial acetic acid saturated with gaseous hydrogen chloride. After 20 hours, the solution is poured into ice/water. The thus-precipitated product is vacuum-filtered and worked up as indicated in Example 17. After chromatography of the crude product on silica gel with acetone/hexane, 215 mg. of 17α-ethinyl-6-chloro-11β-fluoro-17β-hydroxy-4,6-androstadien-3-one is obtained as a foamy product. UV: $\epsilon_{282} = 20,600$ (methanol).

EXAMPLE 21

3.4 g. of 17β-acetoxy-11β-fluoro-4,6-androstadien-3-one is refluxed in 20 ml. of benzene with 3.5 g. of 2,3-dichloro-5,6-dicyano-1,4-benzoquinone for 8 hours. The reaction mixture is diluted with ether and washed successively and repeatedly with 2N sodium hydroxide solution and water. The solution is dried over sodium sulfate. The crude product is chromatographed on silica gel with acetone/hexane, thus obtaining 1.2 g. of 17β-acetoxy-11β-fluoro-1,4,6-androstatrien-3-one. UV: $\epsilon_{298} = 11,900$ (methanol).

EXAMPLE 22

250 mg. of trimethyl sulfoxonium iodide in 8 ml. of dimethyl sulfoxide is agitated for 20 minutes under nitrogen with 48 mg. of pulverized sodium hydroxide. Then, 420 mg. of 17β-acetoxy-11β-fluoro-1,4,6-androstadien-3-one is added. After 3 hours, the reaction mixture is stirred into acetic water. The precipitate is vacuum-filtered, dried, and dissolved in a mixture of 3 ml. of pyridine and 1.5 ml. of acetic anhydride to effect reacetylation. After 30 minutes, the solution is introduced into ice/water. The precipitate is vacuum-filtered, taken up in methylene chloride, and washed with water. Chromatography of the crude product with acetone/hexane yields 85 mg. of 17β-acetoxy-11β-fluoro-1α,2α-methylene-4,6-androstadien-3-one. UV: $\epsilon_{282} = 17,200$ (methanol).

EXAMPLE 23

Under ice cooling, 0.5 ml. of sulfuryl chloride is added dropwise to 1.5 g. of 17β-acetoxy-11β-fluoro-4-androsten-3-one in 10 ml. of pyridine. The solution is introduced into ice water, the precipitate is vacuum-filtered, taken up in methylene chloride, washed with water, and dried. Chromatography on silica gel with acetone/hexane yields 1.3 g. of 17β-acetoxy-4-chloro-11β-fluoro-4-androsten-3-one. UV: $\epsilon_{255} = 13,700$ (methanol).

EXAMPLE 24

2.5 g. of 11β-fluoro-4-androsten-3,17-dione in 50 ml. of absolute tetrahydrofuran is stirred for 3 hours at room temperature with 6 ml. of triethyl orthoformate and 80 mg. of p-toluenesulfonic acid. The solution is then diluted with ether, 1 ml. of pyridine is added, and the mixture is washed repeatedly with water. After drying, the solvent is distilled off under vacuum, thus obtaining 2.4 g. of 3-ethoxy-11β-fluoro-3,5-androstadien-17-one as an oil.

2.0 g. of 3-ethoxy-11β-fluoro-3,5-androstadien-17-one is dissolved in 120 ml. of absolute ether and added to a Grignard solution of 1.3 g. of magnesium and 7.5 g. of methyl iodide in 30 ml. of ether. The reaction mixture is heated for 5 hours until it boils slightly. Then, the solution is combined with dilute hydrochloric acid and the ether phase is washed successively with sodium bicarbonate solution and water. The crude product is chromatographed on silica gel with acetone/hexane, yielding 1.1 g. of 11β-fluoro-17β-hydroxy-17α-methyl-4-androsten-3-one as a foamy product. UV: $\epsilon_{239} = 16,400$.

EXAMPLE 25

850 mg. of 17β-acetoxy-9-chloro-11β-fluoro-4-androsten-3-one is stirred in 16 ml. of tetrahydrofuran with 2 ml. of tributyltin hydride for 2 hours at room temperature with the addition of 5 mg. of α,α'-azoisobutyrodinitrile. The solution is evaporated under vacuum and worked up as described in Example 1. After purification with the aid of preparative layer chromatography, the yield is 250 mg. of 17β-acetoxy-11β-fluoro-4-androsten-3-one; m.p. 163°–166° (acetone/hexane) (decomposition). UV: $\epsilon_{239} = 16,200$ (methanol).

EXAMPLE 26

At −78°, 20 ml. of hydrogen fluoride is combined with 20 ml. of dimethylformamide, and 1.8 g. of 17β-acetoxy-6α,7α-epoxy-11β-fluoro-4-androsten-3-one is added thereto. The reaction mixture is allowed to stand for 2.5 hours at room temperature and then poured into a mixture of ice/water and a 25% ammonia solution. After the reaction mixture has been worked up as described in Example A, it is chromatographed on silica gel with acetone/hexane, thus obtaining 1.2 g. of 17β-acetoxy-6β,11β-difluoro-7α-hydroxy-4-androsten-3-one as an oily product. UV: $\epsilon_{239} = 16,100$ (methanol).

1.1 g. of 17β-acetoxy-6β,11β-difluoro-7α-hydroxy-4-androsten-3-one is combined in 15 ml. of pyridine under ice cooling with 1.3 ml. of mesyl chloride. The reaction mixture is agitated for 4 hours at room temperature; then, the solution is poured into ice/water, extracted with methylene chloride, and the extract is washed with water, thus obtaining 1.2 g. of 17β-acetoxy-6β,11β-difluoro-7α-mesyloxy-4-androsten-3-one which, as the crude product, is stirred under nitrogen in 45 ml. of dimethylformamide with 4 g. of anhydrous potassium acetate for 5 hours at 125°. The solution is poured into ice/water, the precipitate is vacuum-filtered and washed repeatedly with water. After the crude product has been chromatographed on silica gel with acetone/hexane, the yield is 510 mg. of 17β-acetoxy-6,11β-difluoro-4,6-androstadien-3-one as a foamy product. UV: $\epsilon_{283} = 21,600$ (methanol).

EXAMPLE 27

A solution of 3.0 g. of lithium tri-(tert.-butoxy)-aluminum hydride in 15 ml. of tetrahydrofuran is introduced into 2.0 g. of 11β-fluoro-4-androstene-3,17-dione in 5 ml. of tetrahydrofuran. After 45 minutes, the solution is poured into sulfuric ice water and extracted with methylene chloride. The crude product (1.5 g.) representing a mixture of 11β-fluoro-17β-hydroxy-4-androsten-3-one and 11β-fluoro-4-androstene-3β,17β-diol is stirred for 4 hours at room temperature with 1.8 g. of 2,3-dichloro-4,5-dicyano-1,4-benzoquinone in 50 ml. of dioxane. The solution is diluted with ether, washed repeatedly with 2N sodium hydroxide solution and water, and dried over sodium sulfate. After chromatography on silica gel with acetone/hexane, 1.2 g. of 11β-fluoro-17β-hydroxy-4-androsten-3-one is obtained; m.p. 160°–162°. UV: $\epsilon_{239} = 16,500$ (methanol).

EXAMPLE 28

A solution of 2.3 g. of lithium tri-(tert.-butoxy)-aluminum hydride in 12 ml. of tetrahydrofuran is added to 1.4 g. of 3-ethoxy-11β-fluoro-3,5-androstadien-17-one. After 30 minutes, the solution is combined with sulfuric ice water. The reaction product is extracted with methylene chloride; the solution is washed with water and dried over sodium sulfate. The crude product is chromatographed on silica gel with acetone/hexane, yielding 750 mg. of 11β-fluoro-17β-hydroxy-4-androsten-3-one; m.p. 159°–163°. UV: $\epsilon_{239} = 16,100$ (methanol).

EXAMPLE 29

A solution of 1.8 g. of 17β-acetoxy-11β-fluoro-4-androsten-3-one in 60 ml. of acetone and 12 ml. of water is combined with 2.6 g. of N-chlorosuccinimide; the reaction mixture is allowed to stand for 1 day at room temperature. Then, the solution is diluted with methylene chloride, washed successively with sodium thiosulfate solution and water, and dried over sodium sulfate. Chromatography of the crude product on silica gel with acetone/hexane yields 1.1 g. of 17β-acetoxy-6β-chloro-11β-fluoro-4-androsten-3-one. This product is dissolved in 100 ml. of chloroform and combined with 6 ml. of glacial acetic acid saturated with gaseous hydrogen chloride. The solution is allowed to stand at 0° for 2 hours and then introduced into ice/water. The precipitate is vacuum-filtered, washed with water, and dried. After purification by means of preparative layer chromatography (hexane/ethyl acetate 7 : 3), 530 mg. of 17β-acetoxy-6α-chloro-11β-fluoro-4-androsten-3-one is isolated as an oil. UV: $\epsilon_{236} = 15,400$ (methanol).

EXAMPLE 30

A solution, cooled to 0°, of 2.0 g. of 17β-acetoxy-6-chloro-4,6-androstadien-3-one in 20 ml. of dimethylformamide and 10 ml. of ether is combined with 4.5 ml. of a 1.02-molar solution of chlorine in propionic acid. The solution is allowed to stand for 20 hours at 0° and then introduced into ice/water. The thus-precipitated product is taken up in methylene chloride and the solution washed with sodium thiosulfate solution and water. Chromatography on silica gel with acetone/hexane yields 620 mg. of 17β-acetoxy-4,6-dichloro-11β-fluoro-4,6-androstadien-3-one as an oil. UV: $\epsilon_{298} = 16,700$ (methanol).

EXAMPLE 31

900 mg. of 17β-acetoxy-9-bromo-11β-fluoro-4,6-androstadien-3-one is agitated for 5 hours at room temperature in 16 ml. of tetrahydrofuran with 2 ml. of tributyltin hydride while adding 3 mg. of α,α'-azoisobutyrodinitrile. The solution is worked up as described in Example 1. Chromatography on silica gel with acetone/hexane yields 380 mg. of 17β-acetoxy-11β-fluoro-4,6-androstadien-3-one as a foamy product. UV: $\epsilon_{280} = 26,000$ (methanol).

EXAMPLE 32

500 mg. of 11β-fluoro-17β-hydroxy-4-androsten-3-one is allowed to stand in 2 ml. of pyridine with 1 ml. of propionic acid anhydride for 18 hours at room temperature. The solution is introduced into ice water. The precipitate is vacuum-filtered, dissolved in methylene chloride, washed repeatedly with water, and dried over sodium sulfate. After purification with the aid of preparative layer chromatography (hexane/ethyl acetate 7 : 3), the yield is 460 mg. of 11β-fluoro-17β-propionyloxy-4-androsten-3-one. UV: $\epsilon_{239} = 16,200$ (methanol).

EXAMPLE 33

1.2 g. of 9-chloro-11β-fluoro-4-androstene-3,17-dione is agitated for 2 hours at room temperature in 20 ml. of tetrahydrofuran and 3 ml. of triphenyltin hydride with the addition of 7 mg. of α,α'-azoisobutyrodinitrile. The solution is evaporated under vacuum and worked up as set forth in Example 1. After purification by preparative layer chromatography, 380 mg. of 11β-fluoro-4-androstene-3,17-dione is obtained; m.p. 162°–164°. UV: $\epsilon_{238} = 16,300$ (methanol).

EXAMPLE 34

230 mg. of 17β-acetoxy-9-bromo-11β-fluoro-1,4,6-androstatrien-3-one is stirred at room temperature for 5 hours in 7 ml. of tetrahydrofuran with 1 ml. of triphenyltin hydride while adding 1 mg. of α,α'-azoisobutyrodinitrile. The solution is worked up as disclosed in Example 1. After purification by preparative layer chromatography, 70 mg. of 17β-acetoxy-11β-fluoro-1,4,6-androstatrien-3-one is isolated. UV: $\epsilon_{298} = 11,800$ (methanol).

EXAMPLE 35

1.0 g. of 17β-acetoxy-11β-fluoro-4-androsten-3-one is heated under reflux in 50 ml. of carbon tetrachloride with 450 mg. of N-bromosuccinimide and 50 mg. of dibenzoyl peroxide. The solution is washed successively with water, sodium thiosulfate solution, and water after the reaction has been completed. Then, the reaction product is dried over sodium sulfate.

1.1 g. of crude 17β-acetoxy-6β-bromo-11β-fluoro-4-androsten-3-one is stirred in 4 ml. of dimethylformamide for 5 hours at 100° under nitrogen with 100 mg. of lithium bromide and 150 mg. of lithium carbonate. The reaction mixture is introduced into ice/water. The precipitate is vacuum-filtered, taken up in methylene chloride, washed with water, and dried over sodium sulfate. Purification of the crude product by preparative layer chromatography (hexane/ethyl acetate 7 : 3) yields 550 mg. of 17β-acetoxy-11β-fluoro-4,6-androstadien-3-one as a foamy product. UV: $\epsilon_{280} = 26,000$ (methanol).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 11β-fluoroandrostene of the formula

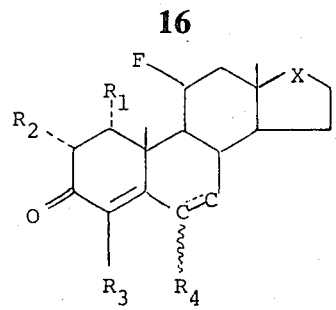

wherein $R_1$ and $R_2$ each are a hydrogen atom or collectively are methylene or a further carbon-to-carbon bond between the C-1 and C-2 carbon atoms; $R_3$ is a hydrogen atom or a chlorine atom, $R_4$ is a hydrogen atom, a fluorine atom or a chlorine atom, C=C is a single or double bond between the C-6 and C-7 carbon atoms, and X is

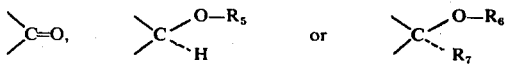

wherein $R_5$ is a hydrogen atom, the acyl radical of a hydrocarbon carboxylic acid of 1–18 carbon atoms, alkyl of 1–4 carbon atoms, or tetrahydropyranyl; $R_6$ is a hydrogen atom or the acyl radical of a hydrocarbon carboxylic acid of 1–18 carbon atoms, and $R_7$ is alkyl, alkenyl or alkynyl of 1–5 carbon atoms, butadiynyl or chloroethynyl.

2. 17β-Acetoxy-11β-fluoro-4-androsten-3-one, a compound of claim 1.

3. 17β-Acetoxy-11β-fluoro-1,4-androstadien-3-one, a compound of claim 1.

4. 11β-Fluoro-17β-hydroxy-4-androsten-3-one, a compound of claim 1.

5. 11β-Fluoro-17β-heptanoyloxy-4-androsten-3-one, a compound of claim 1.

6. 11β-Fluoro-17β-(3'-cyclopentylpropionyloxy)-4-androsten-3-one, a compound of claim 1.

7. 11β-Fluoro-17β-decanoyloxy-4-androsten-3-one, a compound of claim 1.

8. 17β-Benzoyloxy-11β-fluoro-4-androsten-3-one, a compound of claim 1.

9. 11β-Fluoro-17β-methoxy-4-androsten-3-one, a compound of claim 1.

10. 11β-Fluoro-17β-butoxy-4-androsten-3-one, a compound of claim 1.

11. 11β-Fluoro-17β-tetrahydropyranyloxy-4-androsten-3-one, a compound of claim 1.

12. 11β-Fluoro-4-androstene-3,17-dione, a compound of claim 1.

13. 17α-Ethinyl-11β-fluoro-17β-hydroxy-4-androsten-3-one, a compound of claim 1.

14. 17β-Acetoxy-17α-ethinyl-11β-fluoro-4-androsten-3-one, a compound of claim 1.

15. 17α-Ethinyl-11β-fluoro-17β-heptanoyloxy-4-androsten-3-one, a compound of claim 1.

16. 17α-Ethinyl-11β-fluoro-17β-hexadecanoyloxy-4-androsten-3-one, a compound of claim 1.

17. 17β-Acetoxy-11β-fluoro-4,6-androstadien-3-one, a compound of claim 1.

18. 17β-Acetoxy-6-chloro-11β-fluoro-4,6-androstadien-3-one, a compound of claim 1.

19. 11β-Fluoro-4,6-androstadiene-3,17-dione, a compound of claim 1.

20. 17α-Ethinyl-11β-fluoro-17β-hydroxy-4,6-androstadien-3-one, a compound of claim 1.

21. 17α-Ethinyl-6-chloro-11β-fluoro-17β-hydroxy-4,6-androstadien-3-one, a compound of claim 1.

22. 17β-Acetoxy-11β-fluoro-1,4,6-androstatrien-3-one, a compound of claim 1.

23. 17β-Acetoxy-11β-fluoro-1α,2α-methylene-4,6-androstadien-3-one, a compound of claim 1.

24. 17β-Acetoxy-4-chloro-11β-fluoro-4-androsten-3-one, a compound of claim 1.

25. 11β-Fluoro-17β-hydroxy-17α-methyl-4-androsten-3-one, a compound of claim 1.

26. 17β-Acetoxy-6,11β-difluoro-4,6-androstadien-3-one, a compound of claim 1.

27. 17β-Acetoxy-6β-chloro-11β-fluoro-4-androsten-3-one, a compound of claim 1.

28. 17β-Acetoxy-6α-chloro-11β-fluoro-4-androsten-3-one, a compound of claim 1.

29. 17β-Acetoxy-4,6-dichloro-11β-fluoro-4,6-androstadien-3-one, a compound of claim 1.

30. 17β-Acetoxy-11β-fluoro-4,6-androstadien-3-one, a compound of claim 1.

31. 11β-Fluoro-17β-propionyloxy-4-androsten-3-one, a compound of claim 1.

32. 17β-Acetoxy-11β-fluoro-1,4,6-androstatrien-3-one, a compound of claim 1.

33. A process for the production of a compound of formula

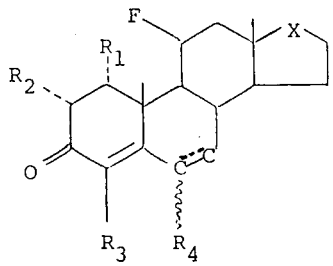

wherein $R_1$ and $R_2$ each are a hydrogen atom or collectively are methylene or a further carbon-to-carbon bond between the C-1 and C-2 carbon atoms; $R_3$ is a hydrogen atom or a chlorine atom, $R_4$ is a hydrogen atom, a fluorine atom or a chlorine atom, C==C is a single or double bond between the C-6 and C-7 carbon atoms, and X is carbonyl, β-hydroxy-methylene or an ester or ether thereof or α-alkyl-β-hydroxy-methylene or an ester thereof, which comprises dehalogenating a corresponding 9α-bromo- or 9α-chloro-11β-fluoro steroid of the formula

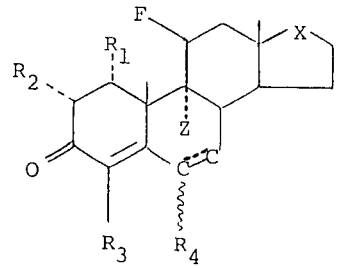

wherein C==C, $R_1$, $R_2$, $R_3$, $R_4$ and X have the values given above and Z is Cl or Br, with a tin hydride in an inert solvent at about room temperature.

34. A process according to claim 33, wherein the 9α-halogen atom is dehalogenated with a trialkyltin hydride or triaryltin hydride.

35. A process according to claim 34, wherein the tin hydride is a triaryltin hydride.

36. A process according to claim 35, wherein the tin hydride is triphenyltin hydride.

37. A method of increasing the androgen blood levels in a patient which comprises administering thereto an androgenically effective amount of a compound of claim 1.

38. A pharmaceutical composition comprising an androgenically effective amount per unit dosage of one or more compounds of claim 1 in admixture with a pharmaceutically acceptable carrier.

* * * * *